(12) United States Patent  
Hudson (10) Patent No.: US 7,474,922 B2
(45) Date of Patent: Jan. 6, 2009

(54) MULTI CHAMBER CAPTURE DETECTION (75) Inventor: Lee Hudson, Lake Jackson, TX (US)

(73) Assignee: BIOTRONIK GmbH & Co. KG (DE)

( * ) Notice: Subject to any disclaimer, the term of this patent is extended or adjusted under 35 U.S.C. 154(b) by 238 days.

(21) Appl. No.: 10/540,309

(22) PCT Filed: Dec. 18, 2003

(86) PCT No.: PCT/EP03/14453

§ 371 (c)(1),
(2), (4) Date: Jan. 9, 2006

(87) PCT Pub. No.: WO2004/056420

PCT Pub. Date: Jul. 8, 2004

(65) Prior Publication Data

US 2006/0136003 A1 Jun. 22, 2006

(51) Int. Cl.
 A61N 1/00 (2006.01)
(52) U.S. Cl. ...................................................... 607/28
(58) Field of Classification Search .................... 607/13, 607/27, 28
See application file for complete search history.

(56) References Cited

U.S. PATENT DOCUMENTS

| 4,033,336 A | 7/1977 | Murawski et al. |
| 4,373,531 A | 2/1983 | Wittkampf et al. |
| 4,537,201 A | 8/1985 | Delle-Vedove et al. |
| 4,686,988 A | 8/1987 | Sholder |
| 4,821,724 A * | 4/1989 | Whigham et al. ............. 607/13 |
| 4,858,610 A | 8/1989 | Callaghan et al. |
| 5,443,485 A | 8/1995 | Housworth et al. |
| 5,607,457 A | 3/1997 | Schüller |
| 5,843,136 A | 12/1998 | Zhu et al. |

* cited by examiner

Primary Examiner—George Manuel
(74) Attorney, Agent, or Firm—Hahn Loeser & Parks LLP (57) ABSTRACT The invention relates to a pacing system, in particular an implantable pacemaker for pacing multiple chambers of the heart and sensing signals from the myocardium of multiple chambers of the heart which will allow the verification of a cardiac evoked response resulting from a delivered charge to the heart tissue comprising:

a preamplifier having a) a DC coupled buffer amplifier first stage, comprising at least one buffer amplifier for each of the at least two electrode inputs, b) a switch matrix following the buffer amplifiers allowing sensing of the differential between any two of the at least two electrode inputs, c) a next stage of differential amplifiers providing gain to either the differential between any two electrode inputs or one input to ground, and d) a next stage filter stage.

20 Claims, 4 Drawing Sheets

FIGURE 3. Capture signal.

FIGURE 4. Non-capture signal.

Fig. 5

MULTI CHAMBER CAPTURE DETECTION

BACKGROUND OF THE INVENTION

The present invention relates to a pacing system, in particular an implantable pacemaker for pacing multiple chambers of the heart and sensing signals from the myocardium of multiple chambers of the heart which will allow the verification of a cardiac evoked response resulting from a delivered charge to the heart tissue comprising: a preamplifier system. The present invention further relates to a method implantable cardiac pacing particularly concerning multichamber pacing and sensing with the capability of performing capture detection in any chamber.

A cardiac pacemaker delivers an electrical stimulus through an implanted lead to the myocardium of a selected area of the heart. If the electrical stimulus is of sufficient energy, the area of myocardium will depolarise and cause a mechanical contraction. The depolarisation immediately following a delivered stimulus is referred to as an evoked response, and the ability to detect this signal is called capture detection or capture verification. This evoked response usually occurs 5-20 ms after the delivery of the stimulation pulse. Typically, the energy output of the pacemaker is set to a level much higher than needed to insure a mechanical contraction. This extra energy consumes battery life, and a system which monitors the energy level needed and provides optimal pacing energy is highly desirable. Monitoring of the needed energy level is critical because the energy threshold to cause a mechanical contraction may change over time. By monitoring each delivered pace for the presence of the evoked response, the System may respond to a change in the threshold level required for a contraction. Verifying an occurrence of an evoked response has been a technical challenge. Due to the characteristics of the tissue-electrode interface of an implanted electrode and the type of pacing waveform typically used, the evoked response signal is usually masked by a much larger polarization voltage which occur after a delivered pace. Many different techniques for overcoming this problem have been proposed. Most of the proposed solutions have not been used in actual practice due to implementation problems.

U.S. Pat. No. 4,858,610 details the use of charge dumping following delivery of the stimulating pulse to decrease lead polarization and also the use of separate pacing and sensing electrodes. U.S. Pat. No. 4,686,988 shows the use of a separate sensing electrode for detecting P-waves in the presence of an atrial stimulation pulse. U.S. Pat. No. 4,373,531 uses pre and post stimulation pulses to neutralize the lead polarization. U.S. Pat. No. 4,537,201 uses an anti-logarithmic amplifier to linearize the exponentially decaying polarization signal, while amplifying only the evoked response signal. U.S. Pat. No. 5,607,457 uses differential sensing between the electrodes in the atrium and ventricle. U.S. Pat. No. 597,957 teaches the sensed cardiac signal is added to either a differentiated or autocorrelated sensed cardiac signal and the difference between the two used to determine the presence of an evoked response. U.S. Pat. No. 5,843,136 teaches the use of an extra capacitor which is switched in series with the DC blocking capacitor to discharge the polarization charge quickly after a stimulus pulse. U.S. Pat. No. 5,443,485 describes a system using an input highpass filter, then bandpass filtering the signal, and finally integrating the bandpassed signal. Many of these approaches are difficult to implement or require pulses increasing battery current consumption. Signal integrity is also an issue with many of these solutions.

Therapies exist needing the capability of pacing multiple chambers of the heart. One pacing therapy for congestive heart failure relies on the placement of electrodes in the right atrium, right ventricle, and the left ventricle. The capability to analyse the signals from many different locations of the heart is also desired. As implantable pulse generators are being developed with greater and greater signal analysis capability, there is a desire to analyse the different signals from many electrode configurations.

SUMMARY OF THE INVENTION

It is therefore an object of the invention to meet the afore mentioned desires.

This object is achieved by a pacing system featuring a preamplifier system comprising a) a DC coupled buffer amplifier (8, 9) first stage, b) a switch matrix (10) following the buffer amplifiers (8, 9) allowing sensing of the differential between any two electrodes adapted to be implanted in the heart, c) a next stage of differential amplifiers (15) providing gain to either the differential between any two electrode inputs or one input to ground, d1) a next stage high pass filter (18) with or without gain with at least one switch (19) capable of discharging the charges transferred across an input capacitor (16) allowing the Output of filter to be reset to analog ground, d2) a next stage low pass filter (21, 22) with or without gain with at least one switch (23) to disconnect the input from the circuit, and d3) a next stage high pass filter (28, 30) with or without gain with at least one switch (31) capable of discharging the charges transferred across the input capacitor allowing the output of the filter to be reset to analog ground.

In an alternative embodiment, the preamplifier system comprises:

a) a DC coupled buffer amplifier stage, b) a switch matrix following the buffer amplifiers allowing sensing of the differential between any two electrodes implanted in the heart, c) a next stage of differential amplifiers providing gain to either the differential between any two electrode Inputs or one Input to ground, and d) a next stage wideband bandpass filter with gain with internal switches capable of discharging the charges transferred across the Input allowing the output of filter to be reset to analog ground.

Thus, the two alternative embodiments differ in features d) or d1), d2), d3), respectively. In the second alternative, the two high pass filters and the low pass filter according to stages d), e) and f) of the first embodiment are replaced by a wideband bandpass filter (stage d) of the second embodiment).

Further components of the first embodiment are:

d4) a next stage low pass filter (35, 36) with or without gain and also with or without switches to disconnect the input and output, e) a next stage being either an analog to digital converter (40) or a narrowband bandpass filter (38) with associated threshold detector (39) under the control of a microprocessor and control logic (41), and f) pacing circuits (42) capable of pacing multiple chambers of the heart with the ability to provide programmable pacing time, a programmable first autoshort time, a programmable sensing time window, und a programmable second autoshort time.

Filters d1 to d4 together form a filter stage of the first embodiment, said filter stage effectively acts as a bandpass filter.

Further components of the second embodiment are e) a next stage being either an analog to digital converter or a narrowband bandpass filter with associated threshold detector under the control of a microprocessor and control logic and f) pacing circuits capable of pacing multiple chambers of the heart with the ability to provide programmable pacing time, a programmable first autoshort time, a programmable sensing time window, und a programmable second autoshort time.

Thus, the two embodiments further differ by the next stage low pass filter according to feature d4) of the first embodiment.

In both embodiments, sensing signals originating from the myocardium are transferred by implantable electrodes, through a connection in a header of the implantable pacemaker, to a sensing circuitry comprising the preamplifier system.

The first components encountered are protection diodes, electromagnetic interference filtering capacitors, and a current limiting resistor. Arranged after the current limiting resistor is a switch connecting the signal from the resistor to the input of a buffer amplifier. The switch is opened during the delivery of the stimulating pulse insuring the amplifier system will not be exposed to a large amplitude signal.

To more adequately detect the evoked response of the myocardium, this buffer amplifier is preferably a FET (field effect transistor) or similar type ultra-high input impedance amplifier. DC coupling to the electrode allows high pass filtering at a later stage in the circuit helping to eliminate unwanted polarization signal affecting the detection of the evoked response.

The buffered signal is then presented a switch matrix. The output of the switch matrix connects to a number of differential amplifiers able to amplify one signal referenced to system ground or the difference between two buffered signals. The output of the differential amplifiers is high pass filtered by a series of low gain first order high pass filters capable of eliminating the DC component quickly after being unblanked. The DC component of one stage is eliminated before the next stage high pass filter is unblanked, The Output of the highpass stage is then sent to the final low pass filter. The output of the final low pass filter is then sent to either a bandpass filter stage or an analog to digital converter for analysis.

The pacing system is preferably capable of delivering several different waveforms. According to a further aspect of the invention several parameters are programmable. The most widely used stimulus is a monophasic pace followed by an autoshort period. The pace amplitude and time are programmable as well as a time delay from the end of the pace to the beginning of the first autoshort. The length of time of the autoshort is also programmable. At the end of the first autoshort, a programmable time detection window is set. During this time the preamplifier system is unblanked and the signal from the bandpass filter is checked for an evoked response. At the end of this detection window, the autoshort function is again invoked for a programmable length of time. If no evoked response occurs, a backup pulse may be delivered to insure a mechanical contraction of the heart.

One method of the invention to determine the presence of an evoked response is to deliver a programmable stimulating monophasic pulse, followed by a programmable autoshort period which is shorter than the time between the end of the pace pulse and the beginning of an evoked response signal. During the delivered pulse and the autoshort period, the switches in front of the buffer amplifiers are open, and immediately at the end of the autoshort period are closed. All blanking switches are also open at this time and all amplifier inputs in the filter stages are set to system ground.

The matrix switches are then closed placing desired signals at the inputs of the differential amplifiers. At this point there will be a polarization voltage present on the electrodes, which will be amplified by the differential amplifier. The switch connecting the output of the differential amplifier to the fast high pass filter is then closed. The charge transferred across the high pass capacitor is then discharged to system ground. The output of the first high pass is then switched to a low pass filter. The low pass filter at this point in time only amplifies the DC offset of the previous amplifier. The signal is then switched to the next high pass filter and the charge transferred across the high pass capacitor in this stage is then discharged to system ground.

The output of the second high pass stage is then sent to the final low pass filter and then switched to the bandpass filter stage. The outputs of the bandpass filters are then connected to programmable threshold detectors. A programmable detection time window is then observed for the presence of an evoked response signal triggering the threshold detector. At the end of the detection window, all blanking switches are opened, and another autoshort is invoked to insure no net charge delivered to the myocardial tissue over times. If no signal was detected during the detection window, a backup pulse will be delivered at a programmable time delay after the end of the window.

The claimed method for determination of the presence of an evoked response includes the steps of:

a) delivering a pacing pulse of programmable amplitude and pulse width, b) performing a first autoshort for a programmable time length, c) unblanking the amplifier system after the first autoshort and sensing an evoked response signal during a programmable sensing time window, d) amplifying the sensed signal by the preamplifier system of Claims 1 or 4, e) sending the amplified signal to the narrowband bandpass filter to allow passage of frequencies contained in the evoked response, f) comparing the signal from the band pass filter to a threshold value, and, if the signal exceeds the threshold value, generating a capture detected signal, or, if the value does not exceed the threshold value a capture detect signal is not generated, and g) blanking the amplifier system at the end of the programmable sensing time window, and invoking the second autoshort for a programmable length of time.

BRIEF DESCRIPTION OF THE SEVERAL VIEWS OF THE DRAWINGS

Further aspects of the invention will become apparent from the following description of preferred embodiments of the invention. These are illustrated in the drawings, wherein.

Figure 1:
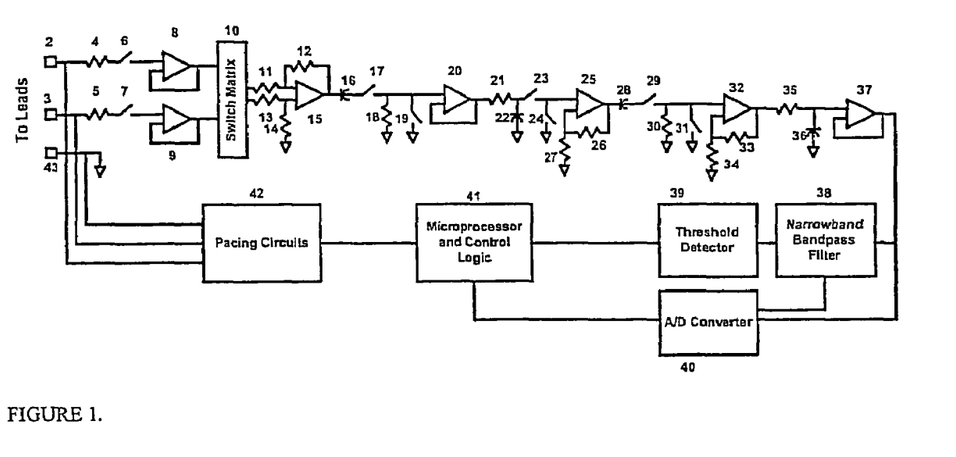
FIG. 1 is a block diagram of a single channel of the system providing the ability to perform capture detection and pacing.

Referring to FIG. 1, a block diagram is illustrated of a sensing circuit capable of capture detection for use in an implantable cardiac pulse generator. The invention allows sensing of both intrinsic cardiac electrograms, and electrograms resulting from a delivered pace in both the atrium and ventricle.

The circuit will allow sensing of the evoked response in either the unipolar mode, where a signal is detected between the tip electrode of the implanted lead and the case of the implantable pulse generator, or in the bipolar mode, where a signal is detected between the tip and ring electrodes of the implanted lead.

Inputs 2 and 3 are the connections to the pacing lead connected to the tip and ring electrodes of an implantable lead. Resistors 4 and 5 are current limiting resistors for both patient safety and circuit protection. Switches 6 and 7 are blanking switches opened during the delivery of a pacing pulse insuring the next stage of the circuit is not exposed to the pacing pulse.

Buffer amplifiers 8 and 9 are FET input or similar type high input impedance amplifiers. These form a unity gain buffer to present very high impedance to the myocardial Signal.

A switch matrix 10 allows the outputs from any buffer amplifier to be switched to any input of the next stage.

Amplifier 15 with associated resistors 11, 12, 13 and 14 form a differential amplifier providing gain to the difference of its two input signals. The input signals may be the output of any of the buffer amplifiers or analog ground.

Capacitor 16 and resistor 18 form a high pass filter. Switch 17 allows the capacitor 16 to be disconnected from the next stage, and switch 19 allows the input to the buffer amplifier 20 to be grounded.

Resistor 21 and capacitor 22 form a low pass filter. Switch 23 allows the output of this filter to be disconnected from the next stage, and switch 24 allows the input to amplifier 25 to be set to ground. Resistors 26 and 27 constitute the gain resistors for amplifier 25.

Capacitor 28 and resistor 30 form the second high pass filter. Switch 29 allows the output of the capacitor 28 to be disconnected from the next stage, and switch 31 allows the Input to amplifier 32 to be Set to analog ground. Resistors 33 and 34 constitute the gain resistors for amplifier 32.

Resistor 35 and capacitor 36 comprise a final low pass filter with amplifier 37. The output of amplifier 37 may then be sent to the narrowband bandpass filter 38 or the analog to digital converter 40. If simple capture detection is desired, the narrowband bandpass filter 38 with a passband of about 22 Hz to 70 Hz would be used to further filter the incoming signal which would then be compared to a predetermined threshold value by the threshold detector 39.

The pacing system also is comprised of control logic and a microprocessor 41 controlling all switches and providing supervisory functions for the pacing circuits 42. The pacing circuits 42 are capable of providing normal pacing and backup pacing for 4 channels.

Figure 2:
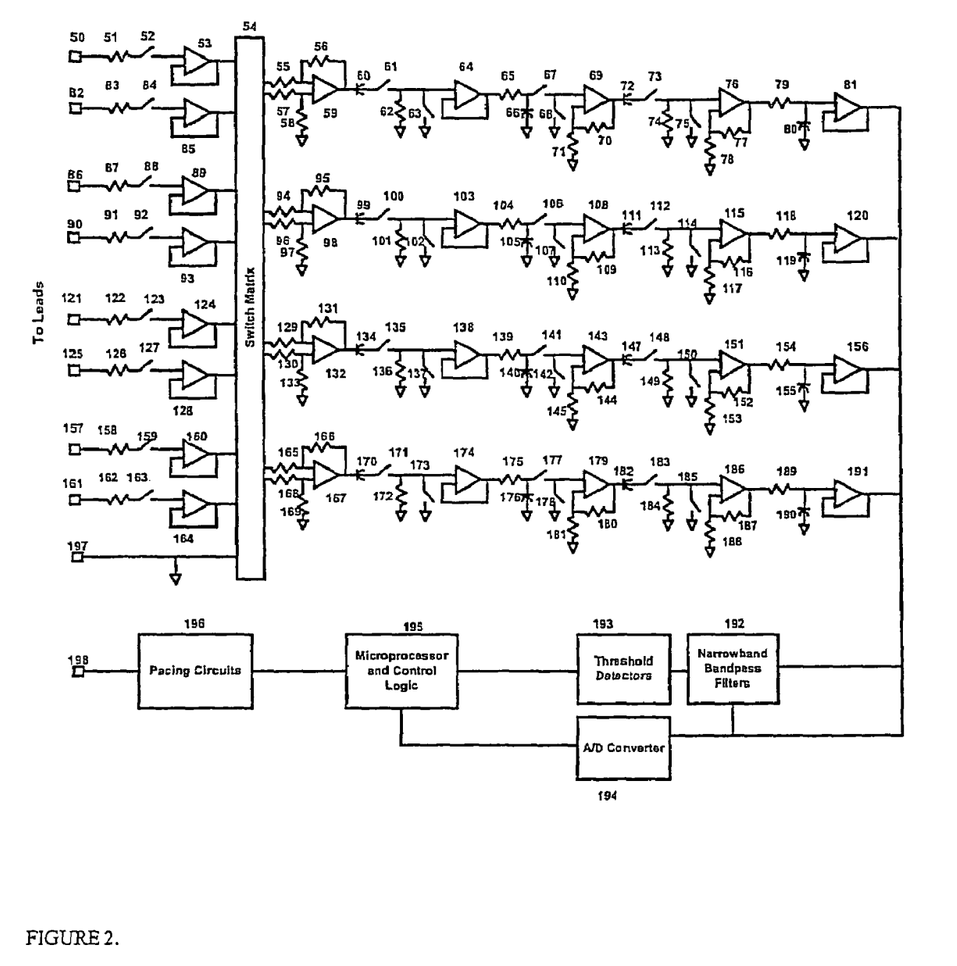
FIG. 2 is a block diagram of the multi chamber implementation of a pacing and sensing system capable of capture detection and signal sensing between any two inputs.

Referring to FIG. 2, shown is the multichannel configuration of the invention. The present configuration allows pacing and sensing in all four chambers of the heart, and will allow the electrograms of any combination of two electrodes in the heart to be analysed.

Inputs to the sensing system (50, 82, 86, 90, 121, 125, 157, 161) are connected to lead electrodes, which may comprise up to four leads each having a tip and ring electrodes for eight input signals.

Input protection resistors (51, 83, 87, 91, 122, 126, 158, 162) provide patient safety as well as overcurrent protection of the integrated circuits.

A first set of blanking switches (52, 84, 88, 92, 123, 127, 159, 163) allows the inputs to the sensing system to be disconnected during the delivery of a pacing pulse.

Buffer amplifiers (53, 85, 89, 93, 124, 128, 150, 164) provide ultra high input impedance to the myocardial Signal, and provide signal buffering to the switch matrix 54. The switch matrix 54 allows the outputs from any buffer amplifier to be switched to any input of the next stage.

Amplifier 59 with associated resistors 55, 56, 57 and 58 form a differential amplifier providing gain to the difference of its two input signals. Amplifiers 98, 132 and 167 and their associated gain resistors are identical to amplifier 59 and corresponding resistors have the same value. The input signals may be the output of any of the buffer amplifiers or analog ground.

Capacitors 60, 99, 134 and 170 and resistors 62, 101, 136 and 172 form high pass filters. Switches 60, 99, 134, and 170 allow the capacitors to be disconnected from the next stage, and switches 63, 102, 137 and 173 allow the input to the buffer amplifiers 64, 103, 138 and 174 to be grounded.

Resistors 65, 104, 139 and 175 and capacitors 66, 105, 140 and 176 form a low pass filter. Switches 67, 106, 141 and 177 allow the output of this filter to be disconnected from the next stage, and switches 68, 107,142 and 178 allows the input to amplifiers 69, 108, 143 and 179 to be set to ground.

Resistors 70 and 71 constitute the gain resistors for amplifier 69, resistors 109 and 110 are the gain resistors for amplifier 108, resistors 144 and 145 constitute the gain resistors for amplifier 143, resistors 180 and 181 are the gain resistors for amplifier 179.

Capacitors 72, 111, 147 and 182 and resistors 74, 113, 149 and 184 form the second high pass filters. Switches 73, 112, 148 and 183 allows the output of the capacitors to be disconnected from the next stage, and switches 75, 114, 150 and 185 allows the inputs to amplifiers 76, 115, 151 and 186 to be set to analog ground. Resistors 77, 78, 116, 117, 152, 153, 187 and 188 constitute the gain resistors for their associated amplifiers.

Resistors 79, 118, 154 and 189 with associated capacitors 80, 119, 155 and 190 form the final low pass filters.

The output of amplifiers 81, 120, 156 and 191 goes either to the narrowband bandpass filters 192 or the analog to digital converter 194. The output of the narrowband bandpass filters may go to either a threshold detector 193 or the analog to digital converter 192. The pacing system also is comprised of control logic and a microprocessor 195 controlling all switches and providing supervisory functions for the pacing circuits 196. The pacing circuits 196 are capable of providing normal pacing and backup pacing for 4 channels.

Figure 3:
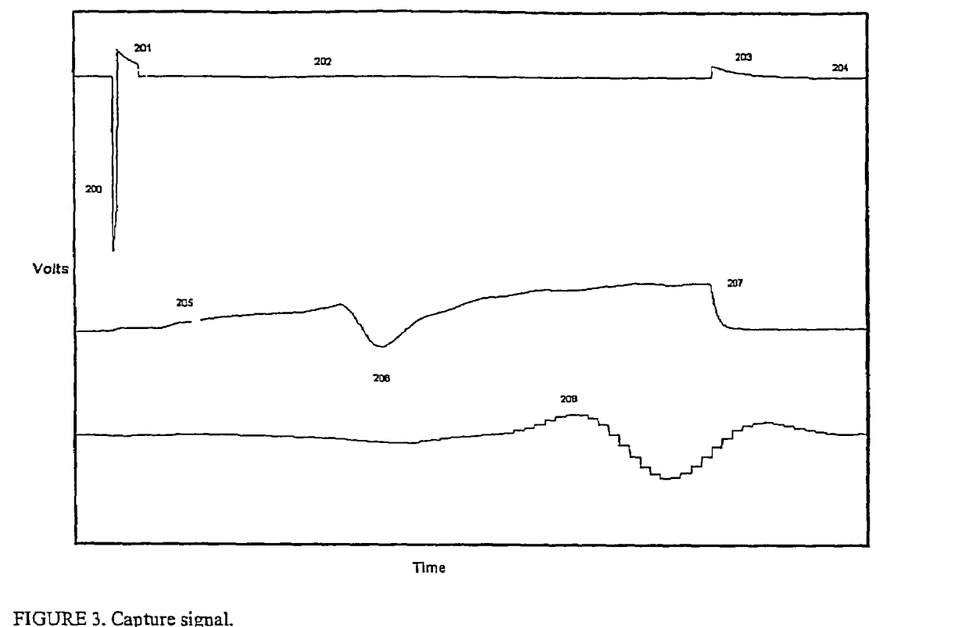
FIG. 3 is a plot of a signal showing three electrical signals, the first the pacing pulse seen by the heart, the second the output of the preamplifier stage and the third the output of the bandpass filter stage for a capture signal.

Referring to FIG. 3, shown are signal traces from three parts of the Invention for a capture signal.

The top trace represents the signal an the tip electrode, corresponding to the Input 2 for FIG. 1.

The second trace represents the Output of the preamplifier system corresponding to the output of amplifier 32 in FIG. 1.

The bottom trace represents the output of the narrowband bandpass filter 36 in FIG. 1.

All subsequent circuit references are from FIG. 1.

Just prior to the delivery of a pacing pulse, switches 6, 7, 17, 23, 29 and 35 are opened, and switches 19, 24 and 31 are closed. Pace is delivered at 200 for the desired amplitude and time, followed by an autoshort period 201 which is shorter than the time delay between the pacing pulse and an evoked response. At the end of the first autoshort period switch 6 is opened and a sensing window time period is allowed 202, and the switch matrix 10 is set to allow the output of buffer amplifier 8 to connect to resistor 11 and analog ground to connected to resistor 13. Switch 17 is then closed allowing the charge transferred across capacitor 16 to be discharged through switch 19. Switch 19 is then opened. Switch 23 is then opened, followed by switch 24 connecting amplifier 25 to the signal path. Switch 29 is then closed allowing the charge transferred across capacitor 29 to be discharged through switch 31. When this charge has been dissipated, switch 31 is opened.

Switch 35 is then closed connecting the preamplifier system to the narrowband bandpass filter 36. At the end of the sensing window time period the second autoshort 203 is invoked to allow any remaining charge at the tissue-electrode Interface to be dissipated. Signal portion 205 m FIG. 3 denotes the closing of switch 35, portion 206 is the evoked response signal from the heart tissue. Signal portion 207 is when the preamplifier system is blanked again by opening and closing the same switches as during the pacing pulse delivery. Signal portion 208 is the output of the narrowband bandpass signal 36 in response to the evoked response signal. This output would then he compared to a predetermined threshold value by the threshold detector 37.

Figure 4:
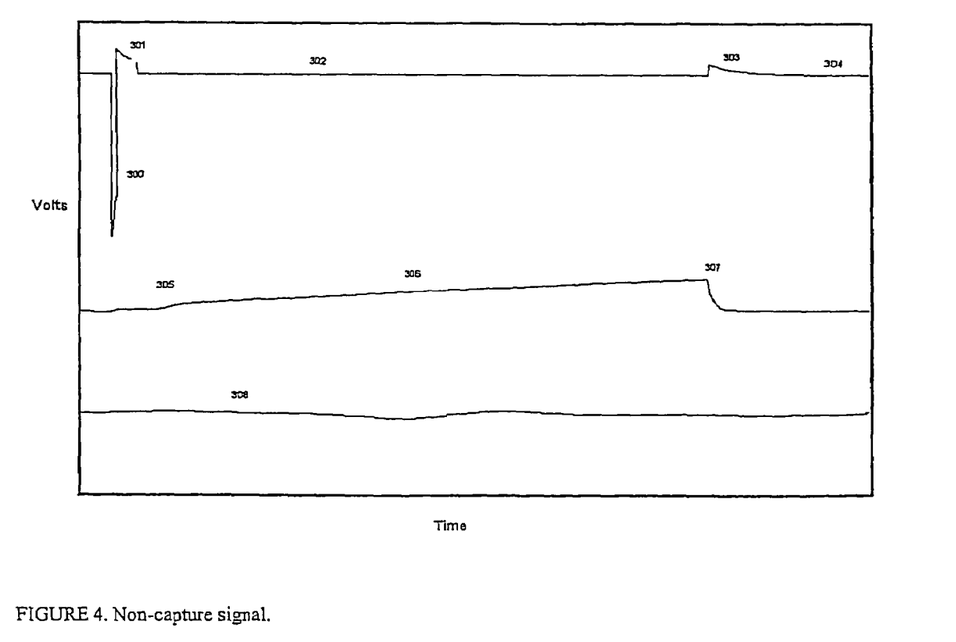
FIG. 4 is a plot of a signal showing three electrical signals, the first the pacing pulse seen by the heart, the second the output of the preamplifier stage and the third the output of the bandpass Filter stage for a non-capture signal.

Referring to FIG. 4, shown are signal traces from the same areas as FIG. 3 except for a non-capture signal. The switch opening and closing sequence is identical to FIG. 3. Since there is no evoked response signal occurring in the sensing window time period, there is no evoked response signal at portion 306 of the middle trace, and also no Signal from the narrowband passband filter. The microprocessor would then send a signal to the pacing circuits to provide a backup pace at a preset time delay after the initial pace.

Figure 5:
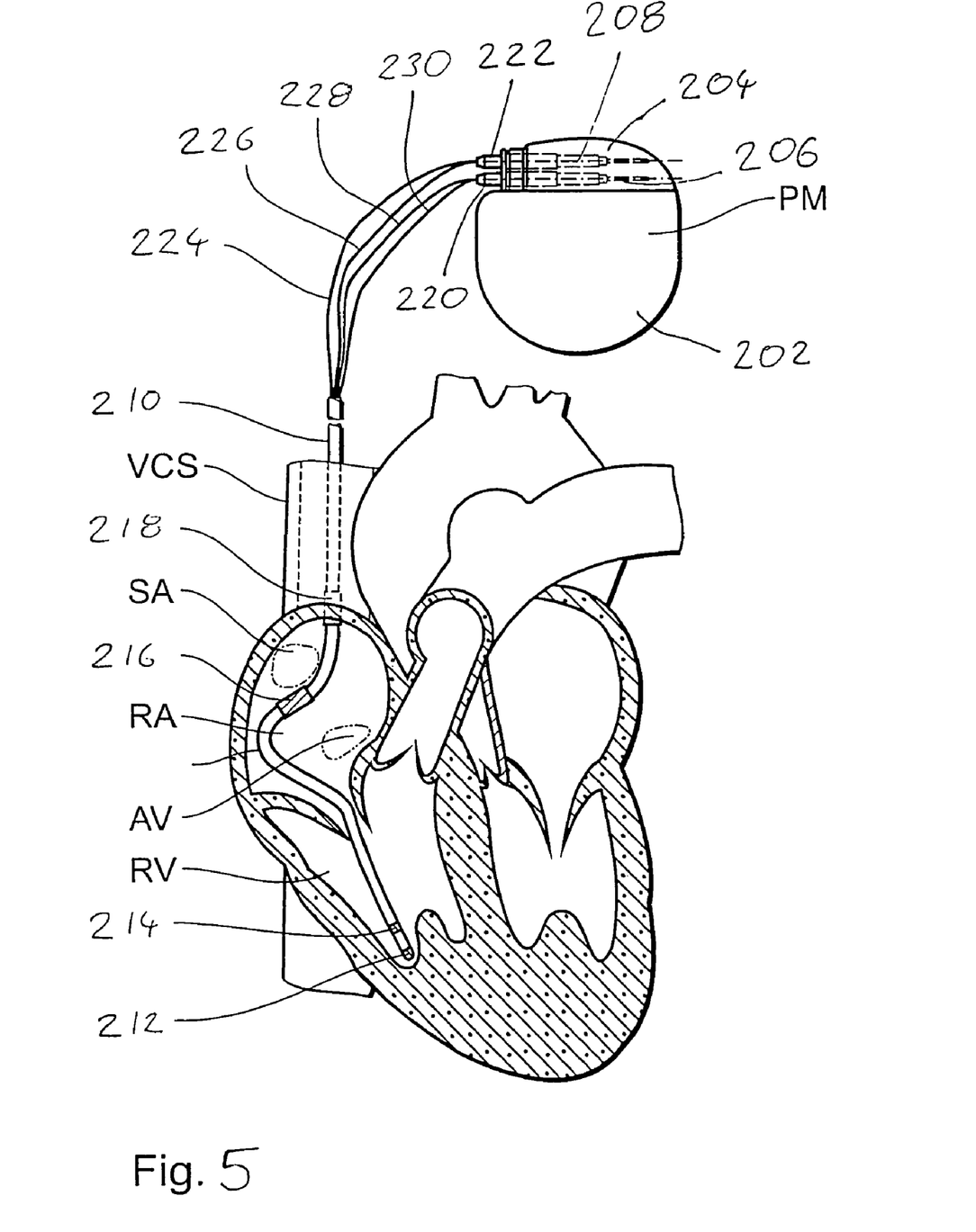
FIG. 5 is representation of a pacemaker in combination with an electrode lead placed in a heart.

FIG. 5 shows a pacing system with a pacemaker (PM) having a housing 202 and a header 204 fixed to the housing 202. Both the housing 202 and the header 204 made from biocompatible material. The housing 202 is made from metal and the header 204 comprises a support structure made from transparent plastic material. The header includes a least one connector 206 for an electrode lead 210. Inside the housing 202, the connector is connected to protection diodes, followed by electromagnetic interference filtering capacitors, and a current limiting resistor (4; 5) as shown in FIG. 1 or 2.

The electrode lead 210 carries four different electrodes, a tip electrode 212 at a distal end of the electrode lead 210 and a ventricular ring electrode 214 having a short distance to the tip electrode 212 and being insulated from the tip electrode 212. Both, tip electrode 212 and ventricular ring electrode 214 are arranged to be placed in a right ventricle RV of a heart.

Two further ring electrodes 216 and 216 are arranged proximally of the electrodes 212 and 214 such that electrodes 216 and 218 will be placed in a right atrium RA of the heart after implantation of electrode lead 210.

At its proximal end, electrode lead 210 is bearing two lead connectors 220 and 222 to be plugged into the connectors 206 and 208 of the header 204.

Electrode lines 224, 226, 228 and 230 form an electrical connection between electrodes 212, 214, 216 and 218 and lead connectors 220 and 222.

Electrode lead 210 is adapted to be implanted in a human heart via vena cava superior VCS.

The invention claimed is:

1. A pacing system for pacing multiple chambers of the heart and sensing signals from the myocardium of multiple chambers of the heart which will allow the verification of a cardiac evoked response resulting from a delivered charge to the heart tissue comprising:
   a preamplifier system circuit having at least two inputs for sensing signals to be picked up by at least two electrodes adapted to pick up the sensing signals, the preamplifier further comprises
   a) a DC coupled buffer amplifier first stage, comprising at least one buffer amplifier for each of the at least two electrode inputs,
   b) a switch matrix following the buffer amplifiers allowing sensing of the differential between any two of the at least two electrode inputs,
   c) a next stage of differential amplifiers providing gain to either the differential between any two electrode inputs or one input to ground, and
   d) a next stage filter stage.

2. The pacing system according to claim 1 wherein the filter stage comprises at least one of
   d1) a first high pass filter with or without gain, having an input capacitor, an output and at least one switch, said switch being capable of discharging charges transferred across the input capacitor allowing the output of the high pass filter to be reset to analog ground,
   d2) a next stage first low pass filter with or without gain, having an input and at least one switch to disconnect the input from the circuit,
   d3) a next stage second high pass filter with or without gain, having an input capacitor, an output and at least one switch capable of discharging the charges transferred across the input capacitor allowing the output of the high pass filter to be reset to analog ground, and
   d4) a next stage second low pass filter with or without gain, having an input and an output.

3. The pacing system according to claim 2, wherein said second low pass filter comprises at least one switch to disconnect the input or the output or both.

4. The pacing system according to claim 1, wherein the pacing system further comprises:
   e) a next stage after the filter stage or the wideband bandpass filter, said next stage being either an analog to digital converter or a narrowband bandpass filter with associated threshold detector under the control of a microprocessor and control logic, and
   f) pacing circuits capable of pacing multiple chambers of the heart with the ability to provide programmable pacing time, a programmable first autoshort time, a programmable sensing time window, und a programmable second autoshort time.

5. The pacing system according to claim 1, comprising a pacemaker (PM) having a housing and a header fixed to the housing, both the housing and the header are made from biocompatible material, the header including a least one connector for an electrode lead, the connector being connected to protection diodes, followed by electromagnetic interference filtering capacitors, and a current limiting resistor which is connected to a switch forming a blanking switch to be opened during the delivery of a pacing pulse, the blanking switch being connected to the preamplifier system.

6. The pacing system according to claim 1, wherein the buffer amplifier is a FET or similar type ultra-high input impedance amplifier.

7. A pacing system for pacing multiple chambers of the heart and sensing signals from the myocardium of multiple chambers of the heart which will allow the verification of a cardiac evoked response resulting from a delivered charge to the heart tissue, the pacing system having a pacing circuit capable of pacing multiple chambers of the heart, the pacing system comprising:
   a preamplifier system having:
   a) a DC coupled buffer amplifier stage,
   b) a switch matrix following the buffer amplifiers allowing sensing of the differential between any two electrodes implanted in the heart,
   c) a next stage of differential amplifiers providing gain to either the differential between any two electrode Inputs or one Input to ground, and
   d) a next stage wideband bandpass filter with gain, having an output and internal switches capable of discharging charges transferred across the Input allowing the output of bandpass filter to be reset to analog ground.

8. The pacing system according to claim 7, wherein the pacing system further comprises
   e) a next stage after the filter stage or the wideband bandpass filter, said next stage being either an analog to digital converter or a narrowband bandpass filter with associated threshold detector under the control of a microprocessor and control logic, and
   f) pacing circuits capable of pacing multiple chambers of the heart with the ability to provide programmable pacing time, a programmable first autoshort time, a programmable sensing time window, and a programmable second autoshort time.

9. The pacing system according to claim 8, comprising a pacemaker (PM) having a housing and a header fixed to the housing, both the housing and the header are made from biocompatible material, the header including a least one connector for an electrode lead, the connector being connected to protection diodes, followed by electromagnetic interference filtering capacitors, and a current limiting resistor, which is connected to a switch forming a blanking switch to be opened during the delivery of a pacing pulse, the blanking switch being connected to the preamplifier system.

10. The pacing system according to claim 9, wherein the buffer amplifier is a FET or similar type ultra-high input impedance amplifier.

11. A method for operating the pacing system according to claim 10 for verifying the capture of the myocardium, the method including the following steps:
   a) delivering a pacing pulse of programmable amplitude and pulse width,
   b) performing a first autoshort for a programmable time length,
   c) unblanking the amplifier system after the first autoshort and sensing an evoked response signal during a programmable sensing time window,
   d) amplifying the sensed signal by a preamplifier system,
   e) sending the amplified signal to the narrowband bandpass filter to allow passage of frequencies contained in the evoked response,
   f) comparing the signal from the band pass filter to a threshold value, and, if the signal exceeds the threshold value, generating a capture detected signal, and
   g) blanking the amplifier system at the end of the programmable sensing time window, and invoking the second autoshort for a programmable length of time.

12. The method according to claim 11, wherein the pacing pulse to be delivered in step a) is programmed to be a monophasic pacing pulse.

13. The method according to claim 12, including the step of:
   h) delivering another pacing pulse of either larger amplitude, longer time or both in delivered at a programmable delay after the second autoshort time, if a capture was not detected in the previous steps.

14. A method for operating the pacing system according to claim 10 for determining the presence of an evoked response of the myocardium, the method including the following steps:
   a) delivering a programmable stimulating monophasic pulse, followed by a programmable autoshort period which is shorter than the time between the end of the pace pulse and the beginning of an evoked response signal,
   b) opening the switches in front of the buffer amplifiers during the delivering of the pulse and the autoshort period, and closing the switches in front of the buffer amplifiers immediately at the end of the auto short period,
   c) at the same time during the delivering of the pulse and the autoshort period opening all blanking switches and setting all amplifier inputs in the filter stages to system ground,
   d) closing the matrix switches of the switch matrix and placing sensed signals at the inputs of the differential amplifiers,
   e) closing the switch connecting the output of the differential amplifier to the fast high pass filter,
   f) discharging the charge transferred across the high pass capacitor to system ground, The output of the first high pass is then switched to a low pass filter,
   g) switching the signal to the next high pass filter,
   h) discharging the charge transferred across the high pass capacitor to system ground,
   i) sending the output of the second high pass stage to the final low pass filter,
   j) switching the output of the final low pass filter, to the bandpass filter stage, and
   k) connecting the outputs of the bandpass filters to programmable threshold detectors.

15. The method according to claim 14, further comprising the steps of:
   l) observing a programmable detection time window for the presence of an evoked response signal triggering at least one threshold detector of the threshold detectors,
   m) opening all blanking switches at the end of the detection window, and
   n) invoking another autoshort to insure no net charge delivered to the myocardial tissue over times.

16. The method according to claim 14, further comprising the step of delivering a backup pulse at a programmable time delay after the end of the window, if no signal was detected during the detection window.

17. A method for operating a pacing system for verifying the capture of the myocardium, the method including the following steps:
   a) delivering a pacing pulse of programmable amplitude and pulse width,
   b) performing a first autoshort for a programmable time length,
   c) unblanking the amplifier system after the first autoshort and sensing an evoked response signal during a programmable sensing time window, d) amplifying the sensed signal by a preamplifier system having a DC coupled buffer amplifier first stage connected to a switch matrix, e) sending the amplified signal to the narrowband bandpass filter to allow passage of frequencies contained in the evoked response, f) comparing the signal from the band pass filter to a threshold value, and, if the signal exceeds the threshold value, generating a capture detected signal, and g) blanking the amplifier system at the end of the programmable sensing time window, and invoking the second autoshort for a programmable length of time.

18. A method for operating a pacing system for determining the presence of an evoked response of the myocardium, the method including the following steps:

a) delivering a programmable stimulating monophasic pulse, followed by a programmable autoshort period which is shorter than the time between the end of the pace pulse and the beginning of an evoked response signal, b) opening switches connected to the input of buffer amplifiers during the delivering of the pulse and the autoshort period, and closing the switches connected to the input of the buffer amplifiers immediately at the end of the autoshort period, c) at the same time during the delivering of the pulse and the autoshort period opening all blanking switches and setting all amplifier inputs in the filter stages to system ground, d) closing the matrix switches of the switch matrix and placing sensed signals at the inputs of the differential amplifiers, e) closing the switch connecting the output of the differential amplifier to the fast high pass filter, f) discharging the charge transferred across the high pass capacitor to system ground, The output of the first high pass is then switched to a low pass filter, g) switching the signal to the next high pass filter, h) discharging the charge transferred across the high pass capacitor to system ground, i) sending the output of the second high pass stage to the final low pass filter, j) switching the output of the final low pass filter, to the bandpass filter stage, and k) connecting the outputs of the bandpass filters to programmable threshold detectors.

19. The method according to claim 18, further comprising the steps of:

l) observing a programmable detection time window for the presence of an evoked response signal triggering the threshold detector, m) opening all blanking switches at the end of the detection window, and n) invoking another autoshort to insure no net charge delivered to the myocardial tissue over times.

20. The method according to claim 18, further comprising the step of delivering a backup pulse at a programmable time delay after the end of the window, if no signal was detected during the detection window.

* * * * *